(12) United States Patent
Liu et al.

(10) Patent No.: US 11,905,369 B2
(45) Date of Patent: Feb. 20, 2024

(54) STRONG BASE-INITIATED N-CARBOXYANHYDRIDE RAPID RING-OPENING POLYMERIZATION METHOD

(71) Applicant: East China University of Science and Technology, Shanghai (CN)

(72) Inventors: Runhui Liu, Shanghai (CN); Yueming Wu, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 678 days.

(21) Appl. No.: 17/058,739

(22) PCT Filed: Jun. 13, 2019

(86) PCT No.: PCT/CN2019/091079
§ 371 (c)(1),
(2) Date: Nov. 25, 2020

(87) PCT Pub. No.: WO2019/238090
PCT Pub. Date: Dec. 19, 2019

(65) Prior Publication Data
US 2021/0155752 A1    May 27, 2021

(30) Foreign Application Priority Data
Jun. 14, 2018 (CN) .......................... 201810614799.1

(51) Int. Cl.
| | | |
|---|---|---|
| C08G 69/10 | (2006.01) | |
| C08G 69/16 | (2006.01) | |
| C08G 69/20 | (2006.01) | |
| C07K 14/00 | (2006.01) | |
| C07K 1/00 | (2006.01) | |

(52) U.S. Cl.
CPC ............. *C08G 69/10* (2013.01); *C08G 69/16* (2013.01); *C08G 69/20* (2013.01); *C07K 1/00* (2013.01); *C07K 14/001* (2013.01)

(58) Field of Classification Search
None
See application file for complete search history.

(56) References Cited

FOREIGN PATENT DOCUMENTS

| CN | 101544684 A | 9/2009 |
|---|---|---|
| CN | 102617851 A | 8/2012 |
| CN | 105440222 A | 3/2016 |
| WO | 0194379 A2 | 12/2001 |

OTHER PUBLICATIONS

Peng, Ring Opening Polymerization of Amino Acid N-Carboxyanhydrides Catalyzed by Rare Earth Catalysts; Journal of Polymer Science Part A: Polymer Chemistry 2012, vol. 50 pp. 1076-1085. (Year: 2011).*
Lu, Hexamethyldisilazide-Mediated Controlled Polymerization of Amino Acid N-Carboxyanhydrides; Journal of the American Chemical Society vol. 129 (2007) pp. 14114-14115. (Year: 2007).*
International Search Report dated Sep. 27, 2019 in PCT/CN2019/091079.
Written Opinion dated Sep. 27, 2019 in PCT/CN2019/091079.

* cited by examiner

*Primary Examiner* — David J Buttner
(74) *Attorney, Agent, or Firm* — Ice Miller LLP

(57) ABSTRACT

The present invention relates to a strong base-initiated N-carboxyanhydride rapid ring-opening polymerisation method. Specifically, the method comprises steps of: performing a polymerisation reaction with one or more amino acid N-carboxyanhydride monomers in an organic solvent in the presence of an initiator, so as to form an amino acid polymer, wherein the initiator is selected from the following group: LiHMDS, NaHMDS, KHMDS, or a combination thereof. The method significantly increases the speed of traditional NCA polymerisation and prepares a long-chain polymer, and the prepared amino acid polymer may be used as an anti-bacterial material, an anti-tumour material, a tissue engineering scaffold or a self-assembling material.

14 Claims, 3 Drawing Sheets

STRONG BASE-INITIATED N-CARBOXYANHYDRIDE RAPID RING-OPENING POLYMERIZATION METHOD

CROSS-REFERENCE TO RELATED APPLICATION

This application is a Section 371 of International Application No. PCT/CN2019/091079 filed Jun. 13, 2019, which was published in the Chinese language Dec. 19, 2019, under International Publication No. WO 2019/238090 A1, which claims priority under 35 U.S.C. § 119(b) to Chinese Patent Application No. 201810614799.1 filed Jun. 14, 2018, the disclosures of which are incorporated herein by reference in their entireties.

TECHNICAL FIELD

The invention belongs to the technical field of amino acid polymer synthesis or preparation methods, and particularly relates to a rapid ring-opening polymerization method of N-carboxyanhydride initiated by a strong base, a polypeptide polymer derived from the method, and various biological functional applications thereof.

BACKGROUND TECHNIQUE

Synthetic polypeptide polymers (amino acid polymers) have good biocompatibility, so they have broad application prospects in many fields, including artificial simulation of proteins/peptides, antibacterial agents and antibacterial materials, drugs and gene delivery, stimulus response polypeptides, tissues engineering and other biological engineering. Polypeptides can be synthesized by two methods including solid-phase synthesis and liquid-phase synthesis. The solid-phase synthesis method is difficult to prepare in large quantities due to its long synthesis time, high cost, short synthesis sequence. The liquid-phase synthesis method can obtain N-carboxyanhydrides (NCA) in high ring-opening polymerization yield and low cost, and can prepare different kinds of polypeptide polymers, so it is the most commonly used and most promising.

Commonly used NCA polymerization initiators include primary amines and amine salts, secondary amines, tertiary amines, alcohols, post-transition metal catalysts, hexamethyldisilazane, and the like. Optimized conditions include low temperature, high vacuum, and changing nitrogen flow. However, the polymerization time of traditional initiators is relatively long, which cannot effectively target the polymerization of unstable NCA monomers, and requires strict anhydrous operation to avoid moisture.

Therefore, there is an urgent need in the art to develop an effective method for polymerizing NCA monomers with simple operation and short reaction time.

SUMMARY OF THE INVENTION

In order to overcome the above shortcomings of N-carboxyanhydride (NCA) polymerization method, the present invention provides a method for preparing a polymer by rapid ring-opening polymerization of NCA initiated by a strong base.

The first aspect of the present invention provides a method for preparing an amino acid polymer, comprising the step of polymerizing one or more amino acid N-carboxyanhydride monomers in an organic solvent in the presence of an initiator, so as to form the amino acid polymer; wherein the initiator is selected from the group consisting of LiHMDS, NaHMDS, KHMDS, and a combination thereof.

In another preferred embodiment, the reaction is performed in an environment protected by an inert gas or in an environment without inert gas protection.

In another preferred embodiment, the environment without inert gas protection is an open beaker, flask or various open and non-open reactors commonly used in industry.

In another preferred embodiment, the environment protected by the inert gas is a glove box protected by nitrogen.

In another preferred embodiment, one, two, three, or four types of amino acid N-carboxy anhydride monomers are polymerized.

In another preferred embodiment, the amino acid polymer is a homopolymer or a copolymer.

In another preferred embodiment, the copolymer is a random copolymer or a block copolymer.

In another preferred embodiment, the copolymer is a polymer obtained by copolymerizing two or more monomers in a set ratio.

In another preferred embodiment, when two types of amino acid N-carboxyanhydride monomers are polymerized, the method comprises steps:

firstly, polymerizing one amino acid N-carboxyanhydride monomer in an organic solvent in the presence of an initiator; and adding another amino acid N-carboxyanhydride monomer to carry out the polymerization reaction after completing the above polymerization reaction, so as to form a block amino acid copolymer.

In another preferred embodiment, when three types of amino acid N-carboxyanhydride monomers are polymerized, the method comprises steps:

firstly, polymerizing a first amino acid N-carboxyanhydride monomer in an organic solvent in the presence of an initiator;

adding a second amino acid N-carboxyanhydride monomer to carry out the polymerization reaction after completing the above polymerization reaction of the first amino acid N-carboxyanhydride monomer;

adding a third amino acid N-carboxyanhydride monomer to carry out the polymerization reaction after completing the above polymerization reaction of the second amino acid INT-carboxy anhydride monomer; and forming a block amino acid copolymer.

Correspondingly, when four types of amino acid N-carboxyanhydride monomers are polymerized, in the above method, after the polymerization of the third amino acid N-carboxyanhydride monomer is completed, the fourth amino acid N-carboxyanhydride monomer is added to carry out the polymerization reactionso as to form a block amino acid copolymer.

By analogy, when more types of amino acid N-carboxyanhydride monomers are polymerized, various monomers can be added in order to perform the polymerization reaction.

In another preferred embodiment, when two types of amino acid N-carboxyanhydride monomers are polymerized, the method comprises steps:

mixing two types of amino acid N-carboxyanhydride monomers in an organic solvent; and performing polymerization reaction in the presence of an initiator, so as to form the amino acid copolymer.

Of course, when more (such as three, four, or more) types of amino acid N-carboxyanhydride monomers are polymerized, the method comprises steps:

mixing the various amino acid N-carboxyanhydride monomers in an organic solvent; and performing polymerization reaction in the presence of an initiator, so as to form an amino acid copolymer.

In another preferred embodiment, in the amino acid N-carboxyanhydride monomer, the amino acid is a natural amino acid or an unnatural amino acid.

In another preferred embodiment, the amino acid is selected from the group consisting of glycine, alanine, valine, leucine, isoleucine, phenylalanine, tryptophan, tyrosine, aspartic acid, asparagine, glutamic acid, lysine, glutamine, methionine, serine, threonine, cysteine, proline, histidine, arginine and derivatives derived from the above-mentioned amino acids.

In another preferred embodiment, the derivative derived from the above-mentioned amino acids is a derivative in which the carboxylic acid group on the amino acid is esterified (e.g., benzyl esterification, tert-butyl esterification, methyl esterification, etc.), a derivative in which the hydrogen atom of an amino group on the amino acid is substituted (e.g., substituted with tert-butoxycarbonyl (Boc), benzyloxycarbonyl (Cbz), fluorenylmethoxycarbonyl (Fmoc), etc.), a derivative in which the hydrogen atom of a hydroxyl group on an amino acid is substituted (e.g. substituted with tert-butyl (tBu)), or a derivative in which the hydrogen atom of a free sulfhydryl group on an amino acid is substituted (e.g., substituted with trityl (Trt), benzyl, benzyl ester, etc.).

In another preferred embodiment, the amino acid N-carboxyanhydride monomer is L-type, D-type or DL-type.

In another preferred embodiment, the amino acid N-carboxyanhydride monomer can be α-NCA, β-NCA or γ-NCA.

In another preferred embodiment, the amino acid N-carboxyanhydride monomer is one or more of the compounds represented by formula I:

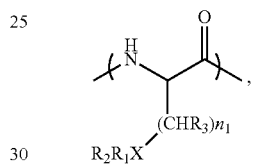

I wherein, $n_1$ is an integer from 0 to 4;

X is absent, azide group ($N_3$), ester group (—(C=O)—O—), amido (—(C=O)—N—), amino (—N—), hydroxyl (—O—), mercapto (—S—), phenyl or 5-6 membered heterocyclic ring;

$R_3$ is hydrogen or C1-C6 alkyl;

$R_1$ and $R_2$ are each independently absent, hydrogen, C1-C6 alkyl, C2-C6 alkenyl, C2-C6 alkynyl, benzyl, tert-butoxycarbonyl, benzyloxycarbonyl, tert-butyl, trityl, or fluorenylmethoxycarbonyl;

one or more hydrogen atoms of $R_1$ and $R_2$ can be substituted by a group selected from the group consisting of halogen, nitro, C1-C6 alkyl, C1-C6 alkoxy, C2-C6 alkenyl, C2-C6 alkenoxy and $CH_3(O—CH_2—CH_2)y$, and y is an integer from 1-6.

In another preferred embodiment, the amino acid N-carboxyanhydride monomer is selected from the following group consisting of: 5-benzyl L-glutamate-N-carboxyanhydride, N-ε-tert-butoxycarbonyl-DL-lysine-N-carboxyanhydride, N-ε-tert-butoxycarbonyl-L-lysine-N-carboxyanhydride, N-ε-tert-butoxycarbonyl-DL-ornithine-N-carboxyanhydride, O-tert-butyl-L-serine-N-carboxyanhydride, DL-norleucine-N-carboxyanhydride, and a combination thereof.

In addition to the configuration specifically given above, the amino acid N-carboxyanhydride monomer according to the present invention can also have other configurations corresponding to various monomers (L type, D type, or DL mixed type). For example, corresponding to 5-benzyl L-glutamate-N-carboxyanhydride, the amino acid N-carboxyanhydride monomer can also be 5-benzyl D-glutamate-N-carboxyanhydride or 5-benzy DL-glutamate-N-carboxyanhydride.

In another preferred embodiment, the organic solvent is selected from the group consisting of tetrahydrofuran, DMF, DMAc, acetonitrile, dioxane, and dimethylsulfoxide.

In another preferred embodiment, the organic solvent is tetrahydrofuran.

The second aspect of the present invention provides an amino acid polymer prepared by the preparation method described in the first aspect.

In another preferred embodiment, the amino acid polymer is a homopolymer, and the structural unit is as follows:

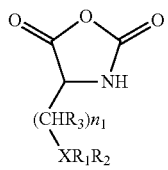

$n_1$, X, $R_3$, $R_1$, and $R_2$ are as defined above.

Compared with the polymer of the same component obtained by other polymerization methods (such as the most commonly used primary amine-initiated polymerization), the polymer does not undergo significant racemization on the chiral structure of the skeleton, and the chiral center and secondary structure are retained.

In another preferred embodiment, the GPC spectrum of homopolymer is single peak, and the molecular weight distribution PDI is 1.1-1.3.

In another preferred embodiment, the homopolymer is poly-5-benzyl L-glutamate-N-carboxyanhydride, poly-N-ε-tert-butoxycarbonyl-DL-lysine-N-carboxyanhydride, poly-N-ε-tert-butoxycarbonyl-L-lysine-N-carboxyanhydride, poly-N-ε-tert-butoxycarbonyl-DL-ornithine-N-carboxyanhydride, poly-O-tert-butyl-L-serine-N-carboxyanhydride, or poly-DL-norleucine-N-carboxyanhydride.

In another preferred embodiment, the amino acid polymer is composed of two or more structural units represented by the following formula,

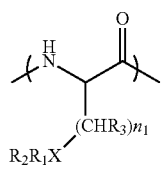

$n_1$, X, $R_3$, $R_1$, and $R_2$ in each structural unit are as defined above, that is, each $n_1$ is an integer from 0 to 4; each X is absent, azide group ($N_3$), ester group (—(C=O)—O—), amido (—(C=O)—N—), amino (—N—), hydroxyl (—O—), mercapto (—S—), phenyl or 5-6 membered heterocyclic ring; each $R_3$ is hydrogen or C1-C6 alkyl;

each $R_1$ and each $R_2$ are independently absent, hydrogen, C1-C6 alkyl, C2-C6 alkenyl, C2-C6 alkynyl, benzyl, tert-butoxycarbonyl, benzyloxycarbonyl, tert-butyl, trityl, or fluorenylmethoxycarbonyl;

one or more hydrogen atoms of $R_1$ and $R_2$ may be substituted by a group selected from the group consisting of halogen, nitro, C1-C6 alkyl, C1-C6 alkoxy, C2-C6 alkenyl, C2-C6 alkenoxy and $CH_3(O-CH_2-CH_2)y$, and y is an integer from 1-6.

In another preferred embodiment, the amino acid polymer is a polymer obtained by copolymerization of two or more monomers in a set ratio.

In another preferred embodiment, the polymer obtained by copolymerization of two or more monomers in a set ratio is obtained by polymerizing a monomer selected from the group consisting of: 5-benzyl L-glutamate-N-carboxyanhydride, N-ε-tert-butoxycarbonyl-DL-lysine-N-carboxyanhydride, N-ε-tert-butoxycarbonyl-L-lysine-N-carboxyanhydride, N-ε-tert-butoxycarbonyl-DL-ornithine-N-carboxyanhydride, O-tert-butyl-L-serine-N-carboxyanhydride, and DL-norleucine-N-carboxyanhydride.

In the polymer obtained by copolymerization of the above two or more monomers in a set ratio, the distribution of the subunit content composition is different from that of the polymer obtained by other polymerization methods from the N-terminal to the C-terminal. Taking the polymerization of two monomers A and B with a monomer ratio of 1:1 (molar ratio) as an example, wherein monomer A has a higher reactivity than monomer B, the polymer composition obtained by the copolymerization is as follows: A in the final polymer chain accounts for 50% (mole percentage), B accounts for 50% (mole percentage), A+B=100%, and from the C-terminal to the N-terminal of the polymer molecular chain, the content of component A gradually decreases and the content of component B gradually increases.

The third aspect of the present invention provides use of the amino acid polymer described in the second aspect as an antibacterial material, an antitumor material, a tissue engineering scaffold, or a self-assembling material.

In another preferred embodiment, the antibacterial material is in the form of a solution or a surface coating.

In another preferred embodiment, the antibacterial objects are microorganisms such as bacteria and fungi, which may include, but are not limited to, *Escherichia coli* (*E. coli*), *Pseudomonas aeruginosa* (*P. aeruginosa*), *Acinetobacter baumannii* (*A. baumannii*), *Enterobacter aerogenes* (*E. aerogenes*), *Klebsiella pneumonia* (*K. pneumoniae*), *Serratia marcescens* (*S. marcescens*), *Entebacter Cloacae* (*E. cloacae*), *Bacillus subtilis* (*B. subtilis*), *Staphylococcus aureus* (*S. aureus*), *Staphylococcus epidermidis* (*S. epidermidis*), *Candida albicans* (*C. albicas*), *Cryptococcus neoformans* (*C. neoformans*). Antibacterial applications include microbial free cells, biofilms, and spores etc.

In another preferred embodiment, the amino acid polymer is used for treating tumors.

In another preferred embodiment, the tumor is selected from the group consisting of melanoma, skin cancer, glioma, mesothelioma, lymphoma, leukemia, breast cancer, ovarian cancer, cervical cancer, glioblastoma, multiple myeloma, prostate cancer, Burkitt lymphoma, head and neck cancer, colon cancer, colorectal cancer, non-small cell lung cancer, small cell lung cancer, esophageal cancer, gastric cancer, pancreatic cancer, hepatobiliary cancer, gallbladder cancer, small intestine cancer, rectal cancer, kidney cancer, bladder cancer, prostate cancer, penile cancer, urinary tract cancer, testicular cancer, vaginal cancer, uterine cancer, thyroid cancer, parathyroid cancer, adrenal cancer, pancreatic endocrine cancer, carcinoid, bone cancer, retinoblastoma, Hodgkin's lymphoma, non-Hodgkin's lymphoma, Kaposi's sarcoma, multicenter Castle man's disease, AIDS-related primary exudative lymphoma, neuroectodermal tumor and rhabdomyosarcoma.

It is to be understood that above each technical feature and each technical feature specifically described hereinafter (as in the examples) within the scope of the present invention may be combined with each other to constitute a new or preferred technical solution. Due to space limitations, those will not be redundantly repeated herein.

DETAILED DESCRIPTION

Figure 1:
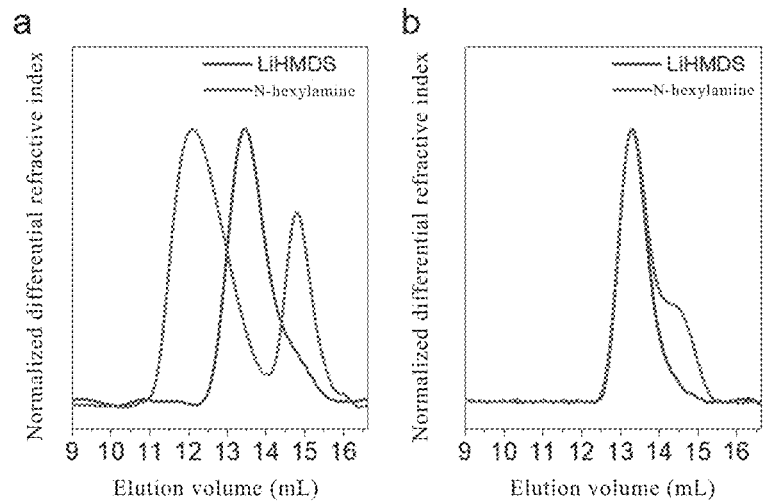
FIG. 1 shows the GPC characterization of a) homopolymer of 5-benzyl L-glutamate-N-carboxyanhydride, and b) homopolymer of N-ε-tert-butoxycarbonyl-DL-lysine-N-carboxyanhydride initiated by LiHMDS and n-hexylamine.

The inventors of the present application have conducted extensive and intensive research and have unexpectedly discovered a strong base-initiated NCA rapid ring-opening polymerization method for preparing an amino acid polymer. The preparation method of the invention greatly improves the speed of traditional NCA polymerization and can prepare long-chain polymers; and it does not need to be operated in a glove box, and the reaction can be successfully operated in an open container without any protection. The present invention has been completed on this basis.

As used herein, "5- to 6-membered heterocyclic ring" refers to a heterocyclic ring having 5-6 ring atoms containing one or two heteroatoms selected from the group consisting of nitrogen atom, sulfur atom, and oxygen atom, such as pyrrolyl, imidazolyl and the like.

Amino Acid N-Carboxyanhydride Monomer of the Present Invention

The amino acid N-carboxyanhydride monomer used in the present invention includes all configurations of the monomer, that is, it can be L-type, D-type, or DL mixed type.

Regarding the structural formula or name of the monomer, the inventor may only exemplarily give a specific configuration or not give a specific configuration. The monomer can also include all other configurations corresponding to the given configuration.

In the amino acid N-carboxyanhydride monomer, the amino acid is a natural amino acid or an unnatural amino acid. The amino acid may be selected from the group consisting of glycine, alanine, valine, leucine, isoleucine, phenylalanine, tryptophan, tyrosine, aspartic acid, asparagine, glutamic acid, lysine, glutamine, methionine, serine, threonine, cysteine, proline, histidine, arginine, and derivatives derived from the above-mentioned amino acids.

The derivative derived from the above-mentioned amino acid is a derivative in which the carboxylic acid group on the amino acid is esterified (e.g., benzyl esterification, tert-butyl esterification, methyl esterification, etc.), a derivative in which the hydrogen atom of an amino group on the amino acid is substituted (e.g., substituted with tert-butoxycarbonyl (Boc), benzyloxycarbonyl (Cbz), fluorenylmethoxycarbonyl (Fmoc), etc.), a derivative in which the hydrogen atom of a hydroxyl group on an amino acid is substituted (e.g. substituted with tert-butyl (tBu)), or a derivative in which the hydrogen atom of a free sulfhydryl group on an amino acid is substituted (e.g., substituted with trityl (Trt), benzyl, benzyl ester, etc.). These derivatives are stable in the polymerization reaction system.

The configuration of the N-carboxyanhydride monomer can be one of L-type, D-type, and DL mixed type. The DL mixed type may be a mixture of L-type and D-type at any ratio. For example, they can be mixed in a ratio of 1:1, but is not limited to this ratio.

The amino acid N-carboxyanhydride monomer can be α-NCA, β-NCA, or γ-NCA.

The side chain of the amino acid N-carboxyanhydride monomer further includes one or more of amino, carboxyl, hydroxyl, mercapto, aliphatic group, and an aromatic group.

The amino acid N-carboxyanhydride monomer is one or more of the compounds represented by formula I:

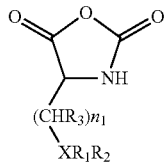

wherein, $n_1$ is an integer from 0 to 4;

X is absent, azide group ($N_3$), ester group (—(C=O)—O—), amido (—(C=O)—N—), amino (—N—), hydroxyl (—O—), mercapto (—S—), phenyl or 5-6 membered heterocyclic ring;

$R_3$ is hydrogen or C1-C6 alkyl;

$R_1$ and $R_2$ are each independently absent, hydrogen, C1-C6 alkyl, C2-C6 alkenyl, C2-C6 alkynyl, benzyl, tert-butoxycarbonyl, benzyloxycarbonyl, tert-butyl, trityl, or fluorenylmethoxycarbonyl;

one or more hydrogen atoms of $R_1$ and $R_2$ can be substituted by a group selected from the group consisting of halogen, nitro, C1-C6 alkyl, C1-C6 alkoxy, C2-C6 alkenyl, C2-C6 alkenoxy and $CH_3(O—CH_2—CH_2)y$, and y is an integer from 1-6.

The monomer may be selected from the group consisting of:

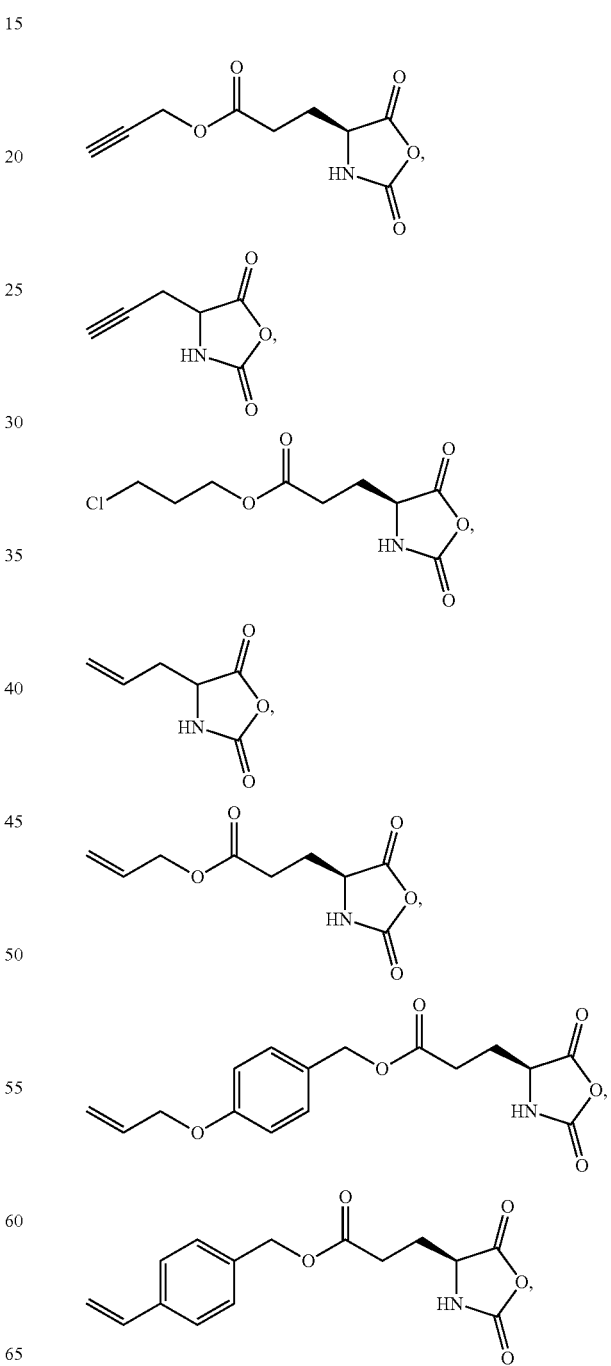

-continued

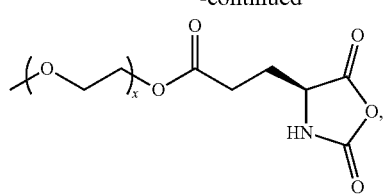

x = 1, 2 or 3

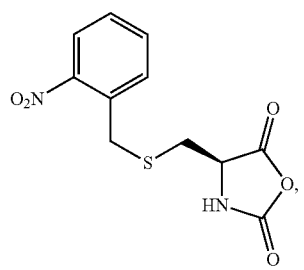

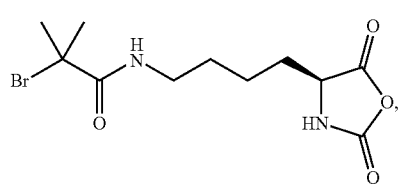

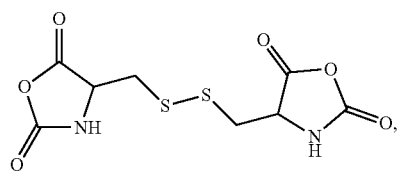

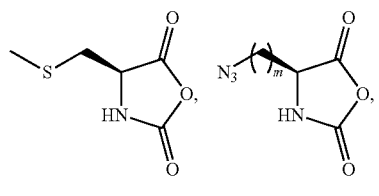

m = 3 or 4

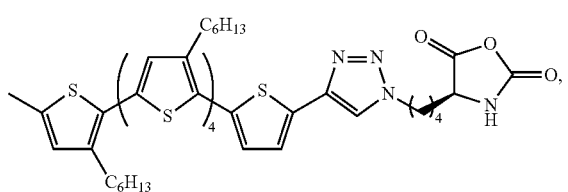

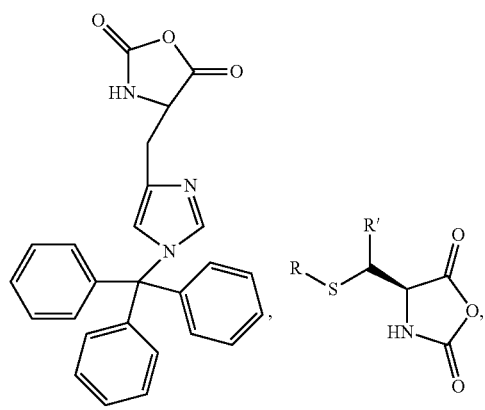

-continued

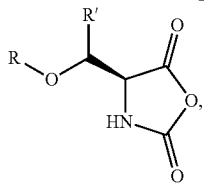

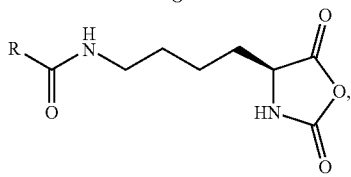

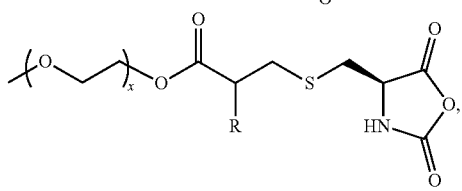

x is an interger from 1 to 9.

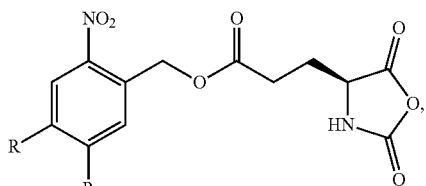

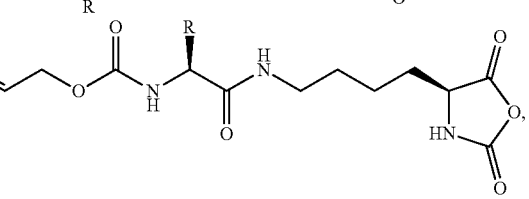

wherein, R' is hydrogen or C1-C6 alkyl; R is hydrogen, C1-C6 alkyl, C1-C6 alkoxy, C1-C6 alkylthio, C1-C6 alkyl-, phenyl, Ac₄Gal, Ac₄Glu or Ac₄Lac.

The amino acid N-carboxyanhydride monomer may be selected from the following group consisting of: 5-benzyl L-glutamate-N-carboxyanhydride, N-ε-tert-butoxycarbonyl-DL-lysine-N-carboxyanhydride, N-ε-tert-butoxycarbonyl-L-lysine-N-carboxyanhydride, N-ε-tert-butoxycarbonyl-DL-ornithine-N-carboxyanhydride, O-tert-butyl-L-serine-N-carboxyanhydride, DL-norleucine-N-carboxyanhydride, and a combination thereof.

Preparation Method of Amino Acid Polymer of the Present Invention

The invention provides a method for preparing an amino acid polymer by rapid ring-opening polymerization of N-carboxyanhydride (NCA) initiated by strong base.

The method comprises the step of polymerizing one or more amino acid N-carboxyanhydride monomers in an organic solvent in the presence of an initiator, so as to form an amino acid polymer.

The strong base initiator includes one or more of lithium hexamethyldisilazide, sodium hexamethyldisilazide, potassium hexamethyldisilazide.

The reaction can be performed in an unprotected apparatus or device (such as an open beaker, flask, or various open reactors commonly used in the industry).

The reaction can also be performed in a nitrogen-protected apparatus or device (such as a glove box).

In the reaction, one amino acid N-carboxyanhydride monomer can be polymerized, or two, three or four different amino acid N-carboxyanhydride monomers can be polymerized.

The type of the obtained amino acid copolymer depends on the type of the amino acid N-carboxyanhydride monomer and the order of addition thereof.

The amino acid polymer is a homopolymer or a copolymer.

The copolymer is a random copolymer or a block copolymer.

The copolymer is a polymer or a block copolymer obtained by copolymerizing two or more monomers in a set ratio.

The organic solvent may be selected from the group consisting of tetrahydrofuran, DMF, DMAc, acetonitrile, dioxane, and dimethylsulfoxide. Tetrahydrofuran is preferred.

The amount of the initiator is determined according to the chain length of the polymer to be prepared.

The polymerization reaction time varies depending on the needs of different monomers, and also depends on the length of the polymer to be prepared.

Preferably, the reaction time is from 1 minute to 24 hours, preferably 1 minute to 12 hours; preferably, 1 minute to 6 hours; more preferably, 1 minute to 1 hour; more preferably, 1-5 minutes.

Depending on the chain length of the desired polymer, the reaction time varies from minutes to hours. For the difference of each polymer, compared with the preparation method using traditional initiator, the reaction rate of the preparation method of the present invention is greatly increased, and the reaction time is greatly reduced.

The reaction is performed at room temperature.

The present invention provides a method for preparing an amino acid polymer, which comprises the step of: polymerizing an N-carboxyanhydride monomer compound I in an organic solvent in the presence of an initiator, so as to form an amino acid polymer II; wherein the initiator is selected from the group consisting of LiHMDS, NaHMDS, KHMDS, and a combination thereof;

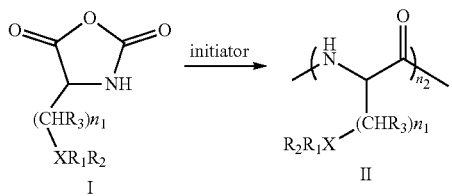

wherein, $n_1$ is an integer from 0 to 4;

X is absent, ester group (—(C═O)—O—), amido (—(C═O)—N—), amino (—N—), hydroxyl (—O—), mercapto (—S—), phenyl or 5-6 membered heterocyclic ring;

$R_1$ and $R_2$ are each independently absent, hydrogen, C1-C6 alkyl, C2-C6 alkenyl, C2-C6 alkynyl, benzyl, tert-butoxycarbonyl, benzyloxycarbonyl, tert-butyl, or fluorenylmethoxycarbonyl;

one or more hydrogen atoms of $R_1$ and $R_2$ can be substituted by a group selected from the group consisting of halogen, nitro, C1-C6 alkyl, C1-C6 alkoxy, C2-C6 alkenyl, C2-C6 alkenoxy and $CH_3(O-CH_2-CH_2)y$, and y is an integer from 1-6;

$n_2$ depends on the amount of initiator.

The invention also provides an open polymerization method, which does not need to be performed in a glove box, and the reaction can be successfully operated in an open container without any protection and without any humidity control.

The Main Advantages of the Invention are as Follows.

The invention provides a strong base-initiated N-carboxyanhydride rapid ring-opening polymerization method for preparing amino acid polymer.

The preparation method of the present invention obtains amino acid polymer by rapid ring-opening polymerization of N-carboxyanhydride initiated by strong base. Compared with traditional NCA polymerization (such as using primary amines and amine salts, post-transition metal catalyst, and hexamethyldisilazane, etc.), the preparation method of the present invention greatly improves the polymerization speed, so that the fastest reaction can be completed within five minutes. Especially for the polymerization of unstable NCA monomers, it has outstanding advantages over the existing polymerization methods. At the same time, the preparation method of the present invention can prepare long-chain polymers (DP>500). In particular, due to the rapidity of the polymerization method of the present invention, there is no need to operate in a glove box, and the polymerization reaction can be successfully operated in an open container without any protection.

The preparation method of the present invention greatly improves the speed of traditional NCA polymerization and can prepare long-chain polymers. It can also be operated without the strict anhydrous environment of a glove box. It can be used in the rapid and easy synthesis of a large number of peptide libraries, for biological activities such as antibacterial activity, cell activity screening, and other peptide polymer function research.

The present invention will be further explained below in conjunction with specific examples. It should be understood that these examples are only used to illustrate the present invention and not to limit the scope of the present invention. The experimental methods without specific conditions in the following examples are usually in accordance with conventional conditions or in accordance with the conditions recommended by the manufacturer. Unless otherwise specified, percentages and parts are percentages by weight and parts by weight.

The experimental materials and reagents used in the following examples can be obtained from commercial sources unless otherwise specified.

Preparation Method of Amino Acid N-Carboxyanhydride Monomer

1. Preparation of 5-benzyl L-glutamate-N-carboxyanhydride

Triphosgene (6.5 g, 22 mmol) was dissolved in dry tetrahydrofuran for use. In an ice-water bath, triphosgene solution was added to a suspension of 5-benzyl L-glutamate (11.8 g, 50 mmol) in dry tetrahydrofuran under the protection of nitrogen, mixed and stirred. Then the mixture was transferred to a 50° C. oil bath and reacted with stirring under nitrogen for about 2 hours. Then the solvent was removed by rotary evaporation under reduced pressure and the residue was dissolved in ethyl acetate, washed with ice water and ice saturate saline, respectively, and dried over anhydrous magnesium sulfate. The crude product was recrystallized three times with dry ethyl acetate and n-hexane to obtain 10.5 g of colorless crystals.

2. Preparation of DL-alanine-N-carboxyanhydride

The experimental method was the same as that in step 1, except that 5-benzyl L-glutamate (11.8 g, 50 mmol) is replaced by DL-alanine (4.45 g, 50 mmol).

3. Preparation of DL-norleucine-N-carboxyanhydride

The experimental method was the same as that in step 1, except that 5-benzyl L-glutamate (11.8 g, 50 mmol) is replaced by DL-norleucine (6.6 g, 50 mmol).

4. Preparation of N-ε-tert-butoxycarbonyl-DL-lysine-N-carboxyanhydride

The experimental method was the same as that in step 1, except that 5-benzyl L-glutamate (11.8 g, 50 mmol) is replaced by N-ε-tert-butoxycarbonyl-DL-lysine (12.3 g, 50 mmol), and α-pinene (20.5 mL, 132 mmol) used as deacid reagent was added.

5. Preparation of N-ε-tert-butoxycarbonyl-L-lysine-N-carboxyanhydride

The experimental method was the same as that in step 4, except that N-ε-tert-butoxycarbonyl-DL-lysine was replaced by N-ε-tert-butoxycarbonyl-L-lysine.

6. Preparation of N-ε-tert-butoxycarbonyl-DL-ornithine-N-carboxyanhydride

The experimental method was the same as that in step 4, except that N-ε-tert-butoxycarbonyl-DL-lysine (12.3 g, 50 mmol) was replaced by N-ε-tert-butoxycarbonyl-DL-ornithine (11.6 g, 50 mmol).

7. Preparation of O-tert-butyl-L-serine-N-carboxyanhydride

The experimental method was the same as that in step 4, except that N-ε-tert-butoxycarbonyl-DL-lysine (12.3 g, 50 mmol) was replaced by O-tert-butyl-L-serine (8.1 g, 50 mmol).

Example 1 Polymerization of 5-benzyl L-glutamate-N-carboxyanhydride Initiated by Lithium Hexamethyldisilazide (LiHMDS)

Lithium hexamethyldisilazide (33.4 mg, 0.2 mmol) was accurately weighed and prepared to a 0.1 M solution in dry tetrahydrofuran (2 mL) for use.

In a nitrogen-protected glove box, 5-benzyl L-glutamate-N-carboxyanhydride (52.6 mg, 0.2 mmol) was accurately weighed and dissolved in dry tetrahydrofuran (1.6 mL) in a reaction flask containing a stir bar.

In a stirred reaction flask, 0.4 mL of 0.1 M of lithium hexamethyldisilazide solution was added. The mixture was stirred for 5 minutes at room temperature in a glove box. The resulting solution was transferred out of the glove box and quenched by adding a drop of formic acid.

Cold petroleum ether (40 mL) was poured into the reaction mixture, and the precipitated white floc was collected by centrifugation, dried in a stream of air, and redissolved in tetrahydrofuran (1.5 mL), and then a large amount of cold petroleum ether was added to precipitate. Such dissolution-precipitation process was repeated three times in total to obtain 35 mg (yield 80%) of a polybenzyl glutamate homopolymer.

As shown in a of FIG. 1, for the polymer obtained by LiHMDS-initiated polymerization identified by a gel permeation chromatography (GPC) method, the molecular weight Mn was 7490 and molecular weight distribution PDI (Mw/Mn) was 1.23; for the polymer prepared by n-hexylamine initiated polymerization as a contrast, it had a bimodal peak, molecular weights Mn were 32640 and 4580, and molecular weight distributions Mw/Mn were 1.27 and 1.04.

Example 2 Polymerization of 5-benzyl L-glutamate-N-carboxyanhydride Initiated by Lithium Hexamethyldisilazide (LiHMDS)(Open Condition)

Lithium hexamethyldisilazide (254 mg, 1.52 mmol) was accurately weighed and prepared to a solution in dry tetrahydrofuran (10 mL) for use.

5-benzyl L-glutamate-N-carboxyanhydride (2.01 g, 7.63 mmol) was accurately weighed and dissolved in dry tetrahydrofuran (66 mL) in a reaction flask containing a stir bar.

The flask was left open to expose the mixed solution to air. The above lithium hexamethyldisilazide solution was added. The mixture was stirred for 5 minutes at room temperature.

A large amount of cold petroleum ether (400 mL) was added to the resulting solution, and the white precipitate was collected by centrifugation and dried by a vacuum pump. The collected solid was redissolved in tetrahydrofuran (30 mL), and then a large amount of cold petroleum ether was added to precipitate. Such dissolution-precipitation process was repeated twice, and 1.47 g of polybenzyl glutamate polymer was obtained.

As measured by gel permeation chromatography (GPC, the molecular weight Mn of the obtained polymer was 6570 and molecular weight distribution PDI was 1.24.

Example 3 Polymerization of N-ε-tert-butoxycarbonyl-DL-lysine-N-carboxyanhydride Initiated by Lithium Hexamethyldisilazide (LiHMDS)

The experimental method was the same as that in Example 1, except that 5-benzyl L-glutamate-N-carboxyanhydride was replaced by N-ε-tert-butoxycarbonyl-DL-lysine-N-carboxyanhydride (26.3 mg, 0.1 mmol), which was dissolved in dry tetrahydrofuran (0.8 mL) instead of dry tetrahydrofuran (1.6 mL); and 0.2 mL of 0.1M LiHMDS solution was added instead of 0.4 mL of 0.1M LiHMDS solution. The reaction time was about 5 minutes.

As shown in b of FIG. 1, the molecular weight Mn of the obtained polymer was 4230 and the molecular weight distribution PDI was 1.19 measured by gel permeation chromatography (GPC).

Example 4 Polymerization of N-ε-tert-butoxycarbonyl-L-lysine-N-carboxyanhydride Initiated by Sodium Hexamethyldsilazide (NaHMDS)

The experimental method was the same as that in Example 1, except that 5-benzyl L-glutamate-N-carboxyanhydride was replaced by N-ε-tert-butoxycarbonyl-L-lysine-N-carboxyanhydride (54.4 mg, 0.2 mmol), which was dissolved in dry tetrahydrofuran (1.9 mL) instead of dry tetrahydrofuran (1.6 mL); and 0.1 mL of 0.1M NaHMDS solution was added instead of 0.4 mL of 0.1M LiHMDS solution. The reaction time was about 15 minutes. As measured by gel permeation chromatography (GPC), the molecular weight Mn of the obtained polymer was 14695 and molecular weight distribution PDI was 1.27.

Example 5 Polymerization of N-ε-tert-butoxycarbonyl-DL-ornithine-N-carboxyanhydride Initiated by Lithium Hexamethyldisilazide (LiHMDS)

The experimental method was the same as that in Example 1, except that 5-benzyl L-glutamato-N-carboxyanhydride was replaced by N-ε-tert-butoxycarbonyl-DL-ornithine-N-carboxyanhydride (129.1 mg, 0.5 mmol), which was dissolved in dry tetrahydrofuran (5.7 mL) instead of dry tetrahydrofuran (1.6 mL); and 0.25 mL of 0.1M LiHMDS solution was added instead of 0.4 mL of 0.1M LiHMDS solution. The reaction time was about 20 minutes. As measured by gel permeation chromatography (GPC), the molecular weight Mn of the obtained polymer was 13810 and molecular weight distribution PDI was 1.23.

Example 6 Binary Polymerization of the Mixture of N-ε-tert-butoxycarbonyl-DL-lysine-N-carboyanhydride and O-tert-butyl-L-serine-N-carboxyanhydride Initiated by Lithium Hexamethyldisilazide (LiHMDS)

The experimental method was the same as that in Example 1, except that 5-benzyl L-glutamate-N-carboxyanhydride was replaced by N-ε-tert-butoxycarbonyl-DL-lysine-N-carboxyanhydride (49.0 mg, 0.18 mmol) and O-tert-butyl-L-serine (3.76 mg, 0.02 mmol) (monomer ratio 9:1). The reaction time was about 5 minutes. As measured by gel permeation chromatography (GPC), the molecular weight Mn of the obtained polymer was 6130 and molecular weight distribution PDI was 1.20.

Example 7 Binary Polymerization of the Mixture of DL-norleucine-N-carboxyanhydride and N-ε-tert-butoxycarbonyl-DL-lysine-N-carboxyanhydride Initiated by Lithium Hexamethyldsilazide (LIHMDS)

The experimental method was the same as that in Example 1, except that 5-benzyl L-glutamate-N-carboxyanhydride was replaced by DL-norleucine-N-carboxyanhydride (7.9 mg, 0.05 mmol) and N-ε-tert-butoxycarbonyl-DL-lysine-N-carboxyanhydride (20.4 mg, 0.075 mmol) (monomer ratio 6:4), which were dissolved in dry tetrahydrofuran (1 mL) instead of dry tetrahydrofuran (1.6 mL); and 0.25 mL of 0.1M LiHMDS solution was added instead of 0.4 mL of 0.1M LiHMDS solution. The reaction time was about 5 minutes. As measured by gel permeation chromatography (GPC), the molecular weight Mn of the obtained polymer was 7241 and molecular weight distribution PDI was 1.25.

Example 8 Block Polymerization of N-ε-tert-butoxycarbonyl-DL-lysine-N-carboxyanhydride and 5-benzyl L-glutamate-N-carboxyanhydride Initiated by Lithium Hexamethyldisilazide (LiHMDS)

The experimental method was the same as that in Example 1, except that 5-benzyl L-glutamate-N-carboxyanhydride was replaced by N-ε-tert-butoxycarbonyl-DL-lysine-N-carboxyanhydride (54.4 mg, 0.2 mmol), and the reaction time was 5 minutes; after the first block reaction was completed, the second block monomer 5-benzyl L-glutamate-N-carboxyanhydride (52.6 mg, 0.2 mmol) was added and the reaction time was about 6 hours. As measured by gel permeation chromatography (GPC), the molecular weight Mn of the obtained first block was 7830 and the molecular weight distribution PDI was 1.20, and the molecular weight Mn of the second block was 11664 and the molecular weight distribution PDI was 1.36.

Example 9 Polymerization of N-ε-tert-butoxycarbonyl-DL-lysine-N-carboxyanhydride Initiated by Lithium Hexamethyldisilazide (LHMDS)

The experimental method was the same as that in Example 3, except that 0.05 mL of 0.1M LiHMDS solution was added instead of 0.4 mL of 0.1 M LiHMDS solution. The reaction time was 15 minutes. As measured by gel permeation chromatography (GPC), the molecular weight Mn of the obtained polymer was 12370 and molecular weight distribution PDI was 1.23.

Comparative Example 1

The experimental method was the same as that in Example 9, except that LiHMDS initiator was replaced by n-hexylamine. The reaction time was about 2-3 days. As shown in b of FIG. 1, gel permeation chromatography (GPC) confirmed that the obtained polymer had bimodal, the molecular weight Mn were 5980 and 2280 and the molecular weight distribution PDI were 1.35 and 1.01.

It could be known from the detection results of a and b in FIG. 1 that the initiation of n-hexylamine brought bimodal peaks, and the polymer obtained by the polymerization initiated by LiHMDS initiator has a huge difference in polymer molecular weight and molecular weight distribution from that obtained by the polymerization initiated by n-hexylamine initiator.

Comparative Example 2

The experimental method was the same as that in Example 9, except that LiHMDS initiator was replaced by HMDS. As a result, it was found that the reaction time was about 5 days.

Example 10 Polymerization of 5-benzyl L-glutamate-N-carboxyanhydride Initiated by Lithium Hexamethyldisilazide (LIHMDS)

The experimental method was the same as that in Example 1, except that dry tetrahydrofuran (0.38 mL) was used instead of dry tetrahydrofuran (1.6 mL), and 0.02 mL of 0.02 M LiHMDS solution was added instead of 0.4 mL of 0.1 M LiHMDS solution, the final monomer concentration was 0.5 M. The reaction time was about 2-4 hours. As measured by gel permeation chromatography (GPC), the molecular weight Mn of the obtained polymer was 111900 and molecular weight distribution PDI was 1.15.

Comparative Example 3

The experimental method was the same as that in Example 1, except that LiHMDS initiator was replaced by n-hexylamine. As a result, it was found that the reaction time was about 7 days.

Comparative Example 4

The experimental method was the same as that in Example 1, except that LiHMDS initiator was replaced by HMDS. As a result, it was found that a large amount of monomer remained after 7 days of reaction.

Example 11 Polymerization of N-ε-tert-butoxycarbonyl-L-lysine-N-carboxyanhydride Initiated by Potassium Hexamethyldisilazide (KHMDS)

The experimental method was the same as that in Example 1, except that 5-benzyl L-glutamate-N-carboxyanhydride was replaced by N-ε-tert-butoxycarbonyl-L-lysine-N-carboxyanhydride (54.4 mg, 0.2 mmol), and 0.1 mL of 0.1 M KHMDS solution was added instead of 0.4 mL of 0.1 M LiHMDS solution. The reaction time was about 15 minutes. As measured by gel permeation chromatography (GPC), the molecular weight Mn of the obtained polymer was 15330 and molecular weight distribution PDI was 1.24.

Example 12 Binary Polymerization of the Mixture of DL-alanine-N-carboxyanhydride and N-ε-tert-butoxycarbonyl-DL-lysine-N-carboxyanhydride Initiated by Lithium Hexamethyldisilazide (LiHMDS)

The experimental method was the same as that in Example 1, except that 5-benzyl L-glutamato-N-carboxyanhydride was replaced by DL-alanine-N-carboxyanhydride (7.9 mg, 0.05 mmol) and N-ε-tert-butoxycarbonyl-DL-lysine-N-carboxyanhydride (20.4 mg, 0.075 mmol) (monomer ratio 6:4), which were dissolved in dry tetrahydrofuran (1 mL) instead of dry tetrahydrofuran (1.6 mL); and 0.25 mL of 0.1M LiHMDS solution was added instead of 0.4 mL of 0.1M LiHMDS solution. The reaction time was about 5 minutes. As measured by gel permeation chromatography (GPC), the molecular weight Mn of the obtained polymer was 7200 and molecular weight distribution PDI was 1.24.

Example 13 Comparison of Subunit Distribution of Polymer Chain Obtained by Binary Polymerization of the Mixture of 5-Benzyl L-Glutamate-N-Carboxyanhydride and N-ε-Tert-Butoxycarbonyl-DL-Lysine-N-Carboxyanhydride Initiated by Different Initiators The polymerization method was the same as that in Example 1, except that 5-benzyl L-glutamate-N-carboxyanhydride was replaced by N-ε-tert-butoxycarbonyl-DL-lysine-N-carboxyanhydride (27.2 mg, 0.1 mmol) and 5-benzyl L-glutamate-N-carboxyanhydride (26.3 mg, 0.1 mmol). Binary polymerization of the mixture of 5-benzyl L-glutamato-N-carboxyanhydride and N-ε-tert-butoxycarbonyl-DL-lysine-N-carboxyanhydride at a ratio of 1:1 was initiated by LiHMDS, n-hexylamine, and HMDS, respectively.

Figure 2:
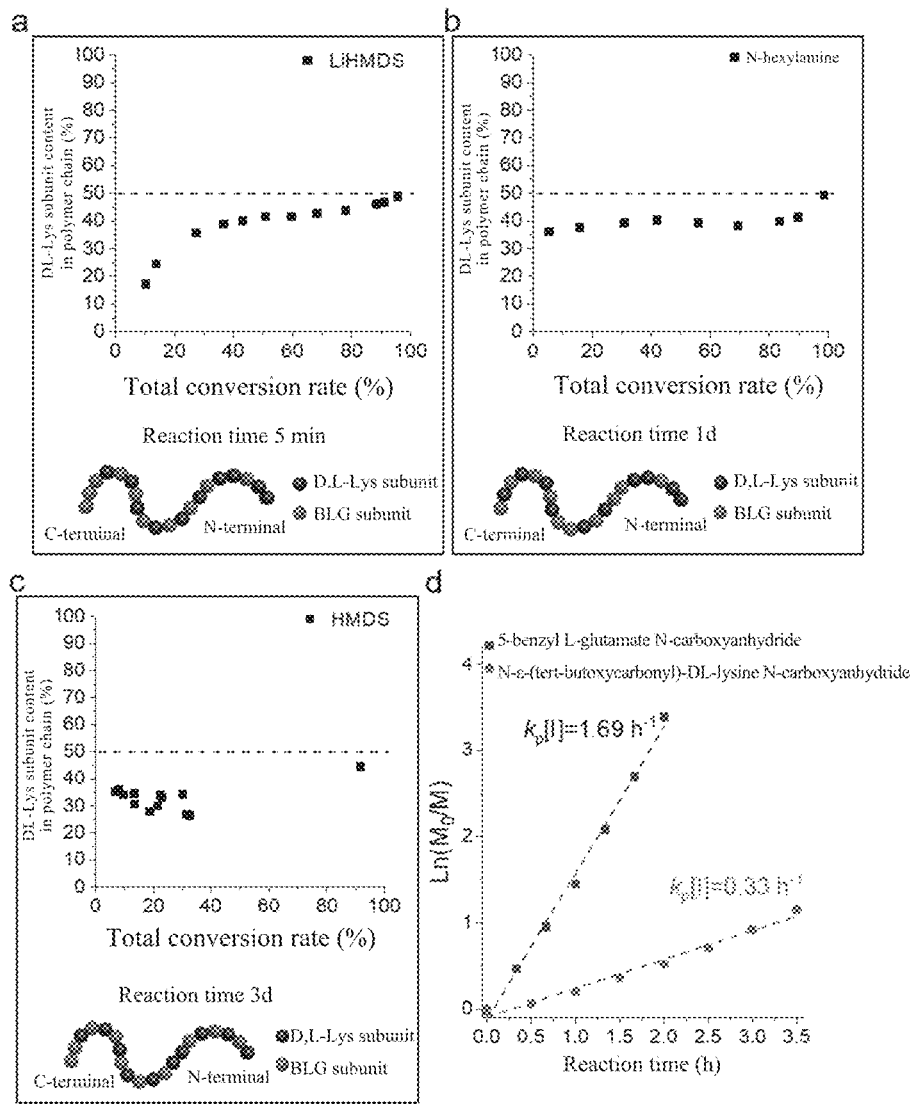
FIG. 2 shows the subunit composition in the polymer chain during the copolymerization of 5-benzyl L-glutamate-N-carboxyanhydride and N-ε-tert-butoxycarbonyl-DL-lysine-N-carboxyanhydride and schematic diagram, wherein: a) LiHMDS initiates polymerization; b) n-hexylamine initiates polymerization; c) HMDS initiates polymerization; and d) dynamic test results for 5-benzyl L-glutamate-N-carboxyanhydride and N-ε-tert-butoxycarbonyl-DL-lysine-N-carboxyanhydride, Kp[I] is polymerization rate constant.

The experimental results were shown in a, b, and c of FIG. 2. Due to different activities of monomers, the distribution and content of subunits of copolymers obtained by different initiator systems were different.

As shown in a of FIG. 2, before the reaction conversion rate reached 30% in the LiHMDS system, the distribution of 5-benzyl L-glutamate subunits (BLG) at the C-terminal was higher than that of N-ε-tert-butoxycarbonyl-DL-lysine subunits (DL-Lys), wherein the content of BLG subunits was more than twice that of DL-Lys. When the reaction conversion rate was 30%-80%, the DL-Lys was evenly distributed and the content accounted for about 40%. After the reaction conversion rate reached 80%, the distribution of DL-Lys subunits at the N-terminal was higher and the content accounted for 50% in the entire polymer chain.

As shown in b of FIG. 2, in the n-hexylamine system, the DL-Lys was relatively evenly distributed at different reaction conversion rates and the content accounted for about 40%, and only when the polymerization reaction was nearly completed, the content of each subunit accounted for 50%.

As shown in c of FIG. 2, in the HMDS system, due to the slow polymerization rate, the conversion rate reached only 40% in two days, and the content of DL-Lys subunits accounted for about 30% of the entire polymer chain. Only when the reaction time continues to extend to the end of the reaction, both monomers are exhausted (monomer decomposition cannot be ruled out), and the content of each subunit eventually accounted for 50%.

Therefore, the different polymerization methods will cause the subunit content in different parts of the copolymer molecular chain to be different, resulting in structural differences in amino acid polymers.

Example 14 Characterization of the Chiral Structure of 5-Benzyl L-Glutamate-N-Carboxyanhydride Initiated by LIHMDS/NaHMDS/KHMDS The synthesis method of polymer used for the specific rotation test was the same as that in Example 1, except that 5-benzyl L-glutamato-N-carboxyanhydride (26.3 mg, 0.1 mmol) and 5-benzyl D-glutamate-N-carboxyanhydride (26.3 mg, 0.1 mmol) were used to replace 5-benzyl L-glutamate-N-carboxyanhydride (50% of D-glutamic acid as an example). The reaction time was about 5 minutes. After the reaction was finished, the reaction solution was transferred to a 50 mL centrifuge tube, and 45 mL of petroleum ether was added to precipitate a white precipitate. The obtained precipitate was separated by centrifugation and redissolved in 1.5 mL of tetrahydrofuran, and then 45 mL of petroleum was added again to precipitate. The synthesized copolymer was purified by three dissolution-precipitation processes. The dried polymer was deprotected to remove benzyl with trifluoroacetic acid/HBr solution, and then 45 mL of frozen ether was added to precipitate a white precipitate. The dissolution-precipitation process was repeated three times to obtain a polymer with side chain carboxyl deprotected polymer. The polymer was tested for the specific rotation after being filtered and lyophilized.

A series of deprotected polymers (D-glutamic acid ratio increased from 0% to 50%) were synthesized and tested for specific rotation at pH 8.0.

Figure 3:
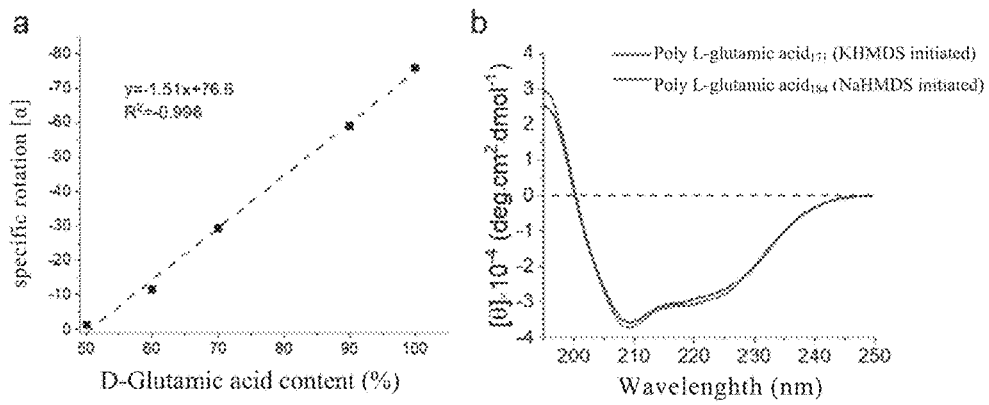
FIG. 3 shows the result of characterizing the chiral structure of the polymer backbone, where a) the relationship between the specific rotation of the polymer and D-glutamic acid content; and b) the secondary structure of the polyglutamic acid characterized by circular dichroism.

As shown in a of FIG. 3, it could be seen from the linear relationship between the specific rotation (Y axis) and the percentage of D-glutamic acid in the deprotected polymer (X axis) that the skeleton racemization was very sensitive to changes in chirality. In addition, it was known from the literature (Polym Sci. 1957, 23, 851-861) that the specific rotation of poly-L-glutamic acid was −80 deg·dm$^{-1}$·g$^{-1}$·mL. The specific rotation of poly-L-glutamic acid synthesized by this method after three tests was in a range of from −78 to −83 deg·dm$^{-1}$·g$^{-1}$·mL. Therefore, LiHMDS initiated 5-benzyl L-glutamate-N-carboxyanhydride with rare skeleton chiral racemization.

The synthesis method of polymer used for the secondary structure test was the same as that in Example 1, except that 0.1 mL of 0.1 M sodium hexamethyldisilazide solution (NaHMDS) or 0.1 mL of 0.1 M potassium hexamethyldisilazide solution (KHMDS) was added instead of 0.4 mL of 0.1 M lithium hexamethyldisilazide solution, and the reaction time was about 15 minutes.

As shown in b of FIG. 3, circular dichroism (CD) spectrum showed that there were one positive peak at 195 nm and two strong negative peaks at 208 nm and 220 nm. It could be seen that polymer of 5-benzyl L-glutamate-N-carboxyanhydride initiated by NaHMDS/KHMDS had a secondary structure of α-helix, which further illustrated that NaHMDS/KHMDS initiated 5-benzyl L-glutamate-N-carboxyanhydride with rare skeleton chiral racemization.

It can be seen from the above:

1. Traditional NCA polymerization, such as the commonly used primary amine initiation, usually takes 2 to 3 days or even longer. However, some NCAs (such as BLG-NCA) is very unstable under traditional NCA polymerization conditions. For example, in DMF, a large amount of monomer is lost within 1-2 hours. After 10 hours, very little monomer is remained, and long-term reaction will cause a lot of side reactions. These uncontrollable side reactions have brought great difficulties to the effectiveness and reproducibility of these peptides, especially in the fields of biomedicine and biomaterial.

However, the present polymerization method has fast polymerization speed and the fastest polymerization can be completed within five minutes. Especially for the polymerization of unstable NCA monomers, the present method has outstanding advantages over the existing polymerization methods, and at the same time greatly inhibits side reactions and can prepare long-chain polymers (DP>500).

2. Traditional NCA polymerization is very sensitive to moisture, so it needs ultra-dry solvent and ultra-dry environment to react. This extremely strict requirement on reaction conditions and reaction environment not only places high requirements on the synthesis technology of researchers, but also greatly hinders the synthetic screening and large-scale synthesis of peptide libraries.

However, the present method can be successfully operated in an open container without the glove box, and by using conventional THF as a solvent without any protection. This greatly reduces the technical and experience requirements of reaction operators, which is conducive to the wide application for more researchers.

Because the new NCA polymerization method provided by the present invention does not need to be operated in a glove box, and does not have the use and space limitations of operating instruments such as a glove box, it is particularly suitable for the synthesis of parallel polymer libraries and the operation of industrially amplified synthesis.

3. Compared with the homopolymer obtained by the polymerization initiated by the traditional initiator, the homopolymer obtained by the present method has a single peak and narrow molecular weight distribution ranging from 1.1 to 1.3 detected by GPC. Moreover, the distribution of the subunits in the copolymer obtained by the present method is different from that in the copolymer obtained by the traditional polymerization method; meanwhile, the polymer obtained by the present method has no obvious skeleton chiral racemization, which is different from the traditional polymerization method (eg., polymerization initiated by the most commonly used primary amine can lead to skeleton chiral racemization).

Example 15 Binary Copolymer of the Mixture of N-ε-Tert-Butoxycarbonyl-DL-Lysine-N-carboxyanhydride and 5-Benzyl L-Glutamate-N-Carboxyanhydride Initiated by Lithium Hexamethyldisilazide (LiHMDS) Used as Solution Antibacterial Material The polymer synthesis method was the same as in Example 1, except that 5-benzyl L-glutamate-N-carboxyanhydride was replaced by N-ε-tert-butoxycarbonyl-DL-lysine-N-carboxyanhydride (27.2 mg, 0.1 mmol) and 5-benzyl L-glutamate-N-carboxyanhydride (26.3 mg, 0.1 mmol) (monomer ratio 5:5 as an example). The reaction time was about 5 minutes. After the reaction was finished, the reaction solution was transferred to a 50 mL centrifuge tube, and 45 mL of petroleum ether was added to precipitate a white precipitate. The obtained precipitate was separated by centrifugation and redissolved in 1.5 mL of tetrahydrofuran, and 45 mL of petroleum was added again to precipitate. The synthesized polymer was purified by three dissolution-precipitation processes. The dried polymer was added to 2 mL of trifluoroacetic acid and shaken gently at room temperature for about 2 hours, and then the excess trifluoroacetic acid was blown off. The obtained viscous liquid was dissolved in 0.5 mL of methanol, and 45 mL of frozen ether was added to precipitate a white precipitate. The dissolution-precipitation process was repeated three times to obtain a side chain amino deprotected random polymer. The deprotected polymer was dissolved again with 5 mL of ultrapure water, filtered, lyophilized and then used for subsequent biological activity test.

The minimum inhibitory concentration (MIC) was tested by using the following method. Bacteria were cultured in a LB liquid medium (Luria-Bertani Broth) in a 37° C. shaker at 150 rpm overnight. The cultured bacterial cells were collected by centrifugation and redistributed in MH (Mueller-Hinton Broth) medium. The absorbance at 600 nm ($OD_{600}$) was read with a microplate reader (when $OD_{600}$ was 1, the concentration of *Staphylococcus aureus* was approximately $1.5 \times 10^9$ cfu/mL). The bacteria solution was diluted with MH medium to $2 \times 10^5$ cfu/mL for later use. The polymer was diluted with MH medium in a 96-well plate at a concentration range of 400 to 3.13 μg/mL. Then 50 μL of the diluted bacterial solution was added to each well so that the total volume of the bacterial solution and the polymer was 100 μL. The plate was shaken slightly for 10 seconds and kept still for 9 hours in a 37° C. mold incubator. Then $OD_{600}$ was read with a microplate reader. 4 wells in the same 96-well plate were added with only MH medium as a negative control, and 4 wells were added with MH medium and the bacterial solution (without polymer) as positive control. Two parallel samples were tested each time and test was repeated twice at different times. The bacterial growth percentage for each well was calculated using the formula $$\left(\% \text{ cell growth} = \frac{A_{600}^{polymer} - A_{600}^{blank}}{A_{600}^{control} - A_{600}^{blank}} \times 100\right).$$

Then the calculated data was plotted into a line chart, with the MIC value being the lowest concentration at which the polymer inhibits bacterial growth.

A series of polymers with different amino acid ratios (ratio from 90% lysine+10% benzyl glutamate to 40% lysine+60% benzyl glutamate) were tested for the lowest inhibitory concentration for various bacteria including methicillin-resistant *Staphylococcus aureus* USA300, methicillin-resistant *Staphylococcus aureus* USA300LAC, methicillin-resistant *Staphylococcus aureus* Mu50, *Bacillus subtilis* BR-151, *Escherichia coli* JM109, *Pseudomonas aeruginosa* ATCC9027, multidrug resistant *Pseudomonas aeruginosa* ATCC15442, sulfamethoxazole and tetracycline naturally resistant *Pseudomonas aeruginosa* O1, *Acinetobacter baumannii* ATCC BAA-747. The obtained MIC results were shown in the following table. The experimental results showed that the polymer containing different proportion of lysine and benzyl glutamate had different antibacterial effects on a variety of bacteria. When the molar percentage of benzyl glutamate (hydrophobic subunit) was 30%-50%, such amino acid polymers had strong and broad-spectrum antibacterial activity.

TABLE 1

Minimum inhibitory concentration (MIC) of amino acid polymers (lysine:benzyl glutamate) on various bacteria, μg/mL

| Bacteria | Polymer (lysine:benzyl glutamate) | | | | | |
|---|---|---|---|---|---|---|
| | 9:1 | 8:2 | 7:3 | 6:4 | 5:5 | 4:6 |
| E. coil JM109 | 12.5 | 12.5 | 25 | 25 | 25 | 50 |
| P. aeruginosa ATCC9027 | 50 | 25 | 12.5 | 12.5 | 12.5 | 25 |
| P. aeruginosa ATCC15442 | 50 | 25 | 25 | 25 | 25 | 50 |
| P. aeruginosa O1 | 25 | 50 | 25 | 25 | 25 | 25 |
| A. baumannii ATCCBAA-747 | 200 | 200 | 50 | 50 | 50 | >200 |
| B. subtilis BR-151 | 3.13 | 3.13 | 6.25 | 6.25 | 6.25 | >200 |
| S. aureus USA300 LAC | 12.5 | 25 | 25 | 25 | 25 | 50 |
| S. aureus USA300 | 25 | 25 | 25 | 25 | 25 | 50 |
| S. aureus mu50 | 12.5 | 25 | 25 | 25 | 25 | 50 |

Example 16 Homopolymer of N-ε-Tert-Butoxycarbonyl-L-Diaminopimelic Acid-N-Carboxyanhydride Initiated by Lithium Hexamethyldisilazide (LiHMDS) Used as an Antifungal Material The polymer synthesis method was the same as that in Example 1, except that 5-benzyl L-glutamate-N-carboxyanhydride was replaced by N-ε-tert-butoxycarbonyl-L-diaminopimelic acid-N-carboxyanhydride. The lowest inhibitory concentrations (MIC) of amino acid polymer on Candida albicans K1 (C. albicans K1) and Cryptococcus neoforman (C. neoformans) were tested. The results were 3.13 μg/mL (C. albicans K1) and less than 1.56 μg/mL (C. neoformans).

Example 17 Binary Copolymer of the Mixture of N-ε-Tert-Butoxycarbonyl-DL-Lysine-N-Carboxyanhydride and 5-Benzyl L-Glutamate-N-Carboxyanhydride Initiated by Lithium Hexamethyldsilazide (LIHMDS) Used as Surface Coating Antibacterial Material The polymer synthesis method was the same as in Example 15, except that triphenylmercaptoethylamine was used for blocking the terminus overnight after the polymerization reaction was finished, and the dried polymer was added to 2 mL of trifluoroacetic acid and 5% (v/v) of triethylsilane instead of 2 mL of trifluoroacetic acid.

The mercapto-terminated amino acid polymer was grafted on the surface of the gold sheet. The surface sterilization test was performed by the following method. The bacteria were cultured in a LB liquid culture medium (Luria-Bertani Broth) in a shaker at 37° C. overnight at 150 rpm. After the culture was completed, 7.5 mL of the bacterial solution was collected from the conical flask and centrifuged at 4000 rpm for 5 min to collect the bacteria, and then re-dispersed into PBS and centrifuged again. After PBS dispersion and centrifugation were repeated three times, the bacteria solution was collected. The absorbance ($OD_{600}$) was read with a microplate reader to quantify the number of colonies. The bacterial solution was diluted with PBS to 1×10⁵ cfu/mL for later use. The prepared polymer antibacterial surface was placed in a 24-well plate with PBS as a control. 80 μL of the bacterial solution having the above concentration was added to the surface of the polymer gold sheet. 80 μL of the bacterial solution was directly added to the well plate as a blank control. PBS was added to the blank well plate to control the humidity. The plate was allowed to stand for 2.5 h in a 37° C. mold incubator and then taken out. 1920 μL PBS was added to the well for dilution, subjected to sonicate for 3 min, and mixed for 2 min with a mixing instrument. 30 μL was aspirated with a pipette and coated on LB agar medium, which then was placed and cultured in a 37° C. mold incubator. After colony counting, the surface antibacterial activity was analyzed. The experimental group was recorded as $C_{sample}$, and the blank control was recorded as $C_{control}$. The antibacterial activity (bacterial killing rate) of the substrate surface was calculated by the following formula:

$$\text{Killing efficacy}(\%) = \left( \frac{C_{control} - C_{sample}}{C_{control}} \times 100 \right)$$

Figure 4:
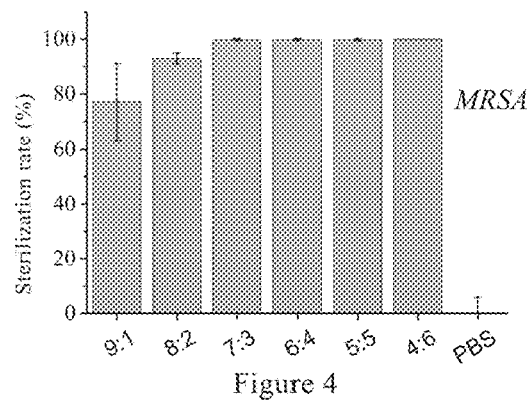
FIG. 4 shows the surface antibacterial activity of amino acid polymers (lysine: benzyl glutamate) on MRSR.

A series of polymers with different amino acid ratios (ratio from 90% lysine+10% benzyl glutamate to 40% lysine+60/ benzyl glutamate) were tested for the Surface sterilization for Methicillin-resistant Staphylococcus aureus (MRSA, Methicillin-resistant Staphylococcus aureus). The obtained results were shown in FIG. 4. The experimental results showed that when the molar percentage of benzyl glutamate (hydrophobic subunit) in such amino acid polymers accounted for 30% to 60%, the polymer surface had a sterilization rate against MRSA of 99.9/and had excellent surface bactericidal efficacy.

Example 18 Binary Copolymer of the Mixture of N-ε-Tert-Butoxycarbonyl-DL-Lysine-N-Carboxyanhydride and 5-Benzyl L-Glutamate-N-Carboxyanhydride Initiated by Lithium Hexamethyldisilazide (LiHMDS) Used as Antitumor Material The polymer synthesis method was the same as in Example 15. The cytotoxicity test (MTT cell proliferation detection) was performed by using the following method. NCI-H460 cells, U87 cells, and B16 cells with a density of 3×10⁴ were seeded in 96-well plates, each well was added with 100 μL. The cells were cultured at 37° C. for 24 hours. After removing the old culture medium, media containing different concentrations of amino acid polymers were added, and three replicates were set for each concentration. After the cells were cultured at 37° C. for 24 hours, 10 μL of MTT solution (5 mg/mL, prepared in PBS) was added to each well. The cells were incubated for another 4 hours and the culture was terminated. The culture supernatant was carefully aspirated from the wells, and 150 μL of DMSO was added to each well. The plate was shaken in a shaker for 10 minutes to fully dissolve the crystals. The same 96-well plate included the cells without any amino acid polymer treatment as a control group and included DMSO only without cells as a blank group. The wavelength of 570 nm was selected, and the absorbance value (OD value) of each well was measured on a microplate reader, and the cell survival rate was calculated based on the following formula:

% cell survival=$(OD^{polymer}-OD^{blank})/(OD^{control}-OD^{blank}) \times 100$.

Based on this, a curve of cell survival rate as a function of amino acid polymer concentration was plotted, and the lowest amino acid concentration ($IC_{50}$) that resulted in 50% mammalian cell death was obtained from the curve.

A series of polymers with different amino acid ratios (ratio from 90% lysine+10% benzyl glutamate to 30% lysine+70% benzyl glutamate) were tested for cytotoxicity for a variety of tumor cells (NCI-H460 lung cancer cells, U87 glioma cells, B16 melanoma cells).

Figure 5:
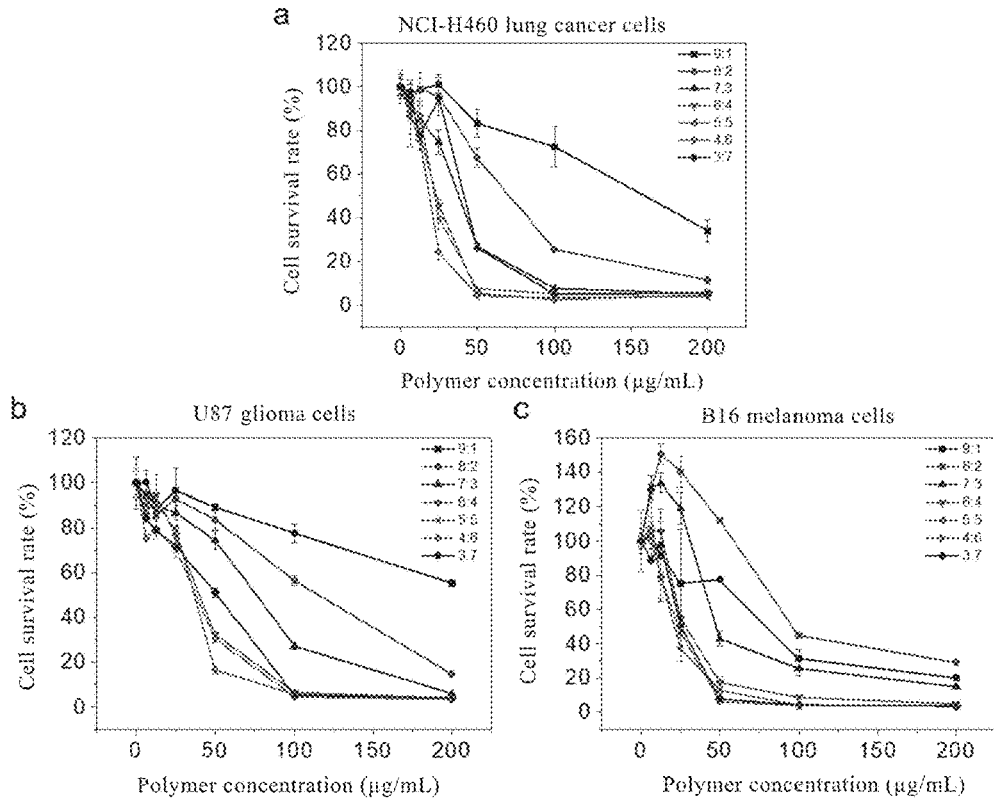
FIG. 5 shows the antitumor activity of amino acid polymers (lysine: benzyl glutamate), a) against NCI-H460 lung cancer cells; b) against U87 glioma cells; and c) against B16 melanoma cells.

The obtained test results for cytotoxicity were shown in FIG. 5. The experimental results proved that the amino acid polymer had anti-tumor effects on three representative tumor cells.

Example 19 Binary Copolymer of the Mixture of N-ε-Tert-Butoxycarbonyl-L-Lysine-N-Carboxyanhydride and 5-Benzyl L-Glutamate-N-Carboxyanhydride Initiated by Lithium Hexamethyldisilazide (LIHMDS) Used as Cell Adhesion Material The polymer synthesis method was the same as in Example 1, except that 5-benzyl L-glutamato-N-carboxyanhydride was replaced by N-ε-tert-butoxycarbonyl-L-lysine-N-carboxyanhydride (27.2 mg, 0.1 mmol) and 5-benzyl L-glutamate-N-carboxyanhydride (26.3 mg, 0.1 mmol)(monomer ratio 5:5 as an example). The reaction time was about 5 minutes. After the reaction was finished, triphenylmercaptoethylamine was used for blocking the terminus overnight, then the reaction solution was transferred to a 50 mL centrifuge tube and 45 mL of petroleum ether was added to precipitate a white precipitate. The obtained precipitate was separated by centrifugation and redissolved in 1.5 mL of tetrahydrofuran, and 45 mL of petroleum was added again to precipitate. The synthesized polymer of the mixture of two or more monomers in a set ratio was purified by three dissolution-precipitation processes. The dried polymer was added to 2 mL of trifluoroacetic acid and 5% (v/v) triethylsilane and shaken gently at room temperature overnight, and then the excess trifluoroacetic acid was blown off. The obtained viscous liquid was dissolved in 0.5 mL of methanol, and 45 mL of frozen ether was added to precipitate a white precipitate. The dissolution-precipitation process was repeated three times to obtain a side chain amino and end mercapto deprotected random polymer. The deprotected polymer was dissolved again with 5 mL of ultrapure water, filtered, lyophilized and then used for subsequent biological activity test.

Figure 6:
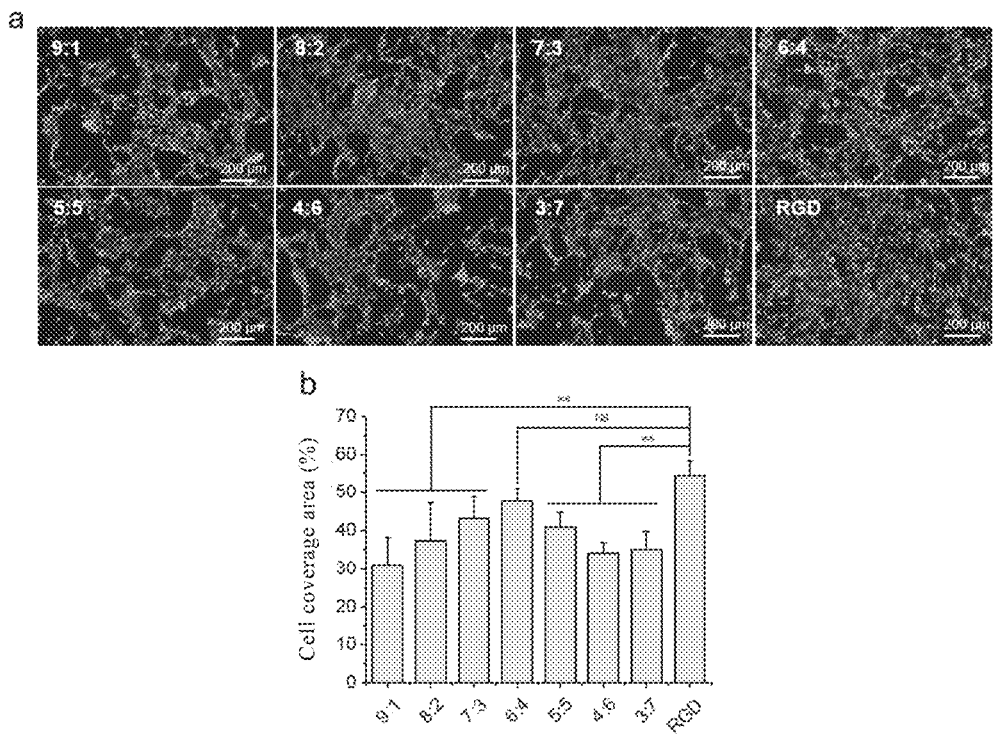
FIG. 6 shows the effect of amino acid polymer (lysine: benzyl glutamate) on cell adhesion and cell growth of mouse embryonic fibroblasts (NIH 3T3), a) fluorescent staining of cells at 48 h under an inverted fluorescence microscope; and b) quantitative analysis of cell adhesion, **$p<0.01$, NS is no significant difference.

The amino acid polymer was grafted on the surface of the glass substrate. The specific method was as follows. 3-aminopropyltriethoxysilane was used as the glass surface amino modifier to modify clean surface-activated glass, and then the aminated glass was modified by PEG, and finally grafted with the amino acid polymer and positive control polypeptide (RGD). The cells were trypsinized and collected in a centrifuge tube and the cell density was adjusted to $8 \times 10^4$ cells/mL. The cells were inoculated on the surface of the amino acid polymer in the well. The polymer surface was placed in a petri dish, and cultured in a 37° C. incubator. After the cells were incubated for 2 hours, the adherence, spreading, and agglomeration of the cells on the polymer surface were observed under an inverted microscope; then the polymer surface adhered with the cells was immersed in the culture medium and cultured for another 24 to 48 hours. The morphology of cell adhesion and growth on the amino acid polymer surface in multiple areas was observed by an inverted fluorescence microscope, and the coverage area (%) of the cell surface was calculated. The experimental results were shown in FIG. 6. On the glass surface grafted with the amino acid polymer, mouse embryonic fibroblasts (NIH 3T3) exhibited different adhesion effects at 48 h. The polymer having a ratio of 6:4 showed a similar cell adhesion effect to the positive control RGD. Cell adhesion was a key step in the action of cells and materials in tissue engineering. Only after adhesion, the cells could undergo a series of behaviors such as proliferation, migration, and differentiation. Therefore, supporting cell adhesion was an essential property for use of biomaterials in tissue engineering.

Example 20 Binary Copolymer of the Mixture of N-ε-Tert-Butoxycarbonyl-L-Lysine-N-Carboxyanhydride and 5-Benzyl L-Glutamate-N-Carboxyanhydride Initiated by Sodium Hexamethyldisilazide (NaHMDS) Used as Self-Assembling Material The polymer synthesis method was the same as in Example 1, except that 5-benzyl L-glutamate-N-carboxyanhydride was replaced by N-ε-tert-butoxycarbonyl-L-lysine-N-carboxyanhydride (21.8 mg, 0.08 mmol) and 5-benzyl L-glutamate-N-carboxyanhydride (31.6 mg, 0.12 mmol) and 0.4 mL of 0.1 M NaHMDS solution was used instead of 0.4 mL of 0.1 M LiHMDS solution. The reaction time was about 5 minutes. After the reaction was finished, the reaction solution was transferred to a 50 mL centrifuge tube and 45 mL of petroleum ether was added to precipitate a white precipitate. The obtained precipitate was separated by centrifugation and redissolved in 1.5 mL of tetrahydrofuran, and 45 mL of petroleum was added again to precipitate. The synthesized polymer of the mixture of two or more monomers in a set ratio was purified by three dissolution-precipitation processes. The dried polymer was added to 2 mL of trifluoroacetic acid and shaken gently at room temperature for 2 h, and then the excess trifluoroacetic acid was blown off. The obtained viscous liquid was dissolved in 0.5 mL of methanol, and 45 mL of frozen ether was added to precipitate a white precipitate. The dissolution-precipitation process was repeated three times to obtain a side chain amino deprotected random polymer. The deprotected polymer was dissolved again with 5 mL of ultrapure water, filtered, lyophilized and then used for subsequent self-assembly test.

The polymer self-assembly structure was prepared by the following method: 1 mg of amphiphilic polymer was dissolved in the corresponding volume of ultrapure water, and prepared as a 0.2 mg/mL or 0.5 mg/mL solution, and the solution was stirred at a medium speed of 390 rpm for 2 h and then kept still for 2 h. The self-assemble solution was filtered using a 0.8 μm filter, and a DLS test was performed.

Figure 7:
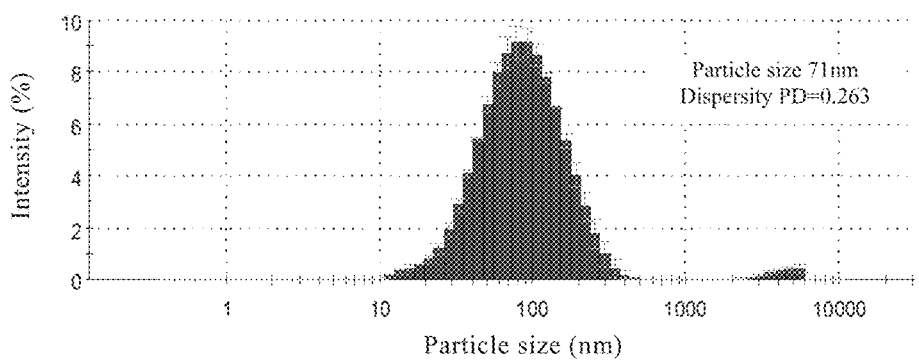
FIG. 7 shows the result of DLS analysis of polymer self-assembly.

The self-assembled samples were tested for particle size and dispersion using dynamic light scattering (DLS). The sample was placed in a PS cuvette. The volume of each test sample was about 1.5 mL. Each sample was repeatedly tested three times. The test temperature was 25° C. and the test angle was set to 90°. Data were processed using cumulative analysis of experimental correlation functions, and the diffusion coefficient was calculated by using Stokes-Einstein equation. The results of the DLS experiment were shown in FIG. 7. When the ratio of lysine to benzyl glutamate was 4:6, the amino acid polymer forms a relatively stable self-assembled structure in water with a particle size of 71 nm and a dispersity PD of 0.263.

All documents mentioned in the present invention are cited as references in this application, as if each document is individually cited as a reference. In addition, it should be understood that after reading the above teaching content of the present invention, those skilled in the art can make various changes or modifications to the present invention, and these equivalent forms also fall within the scope defined by the appended claims of the present application.

The invention claimed is:

1. A method for preparing an amino acid polymer comprising the step of:
   polymerizing one or more amino acid N-carboxyanhydride monomers in an organic solvent in the presence of an initiator, so as to form the amino acid polymer;
   wherein the initiator is selected from the group consisting of LiHMDS, NaHMDS, KHMDS, and a combination thereof.

2. The method of claim 1, wherein the reaction is performed in an environment protected by an inert gas.

3. The method of claim 1, wherein one, two, three, or four types of amino acid N-carboxyanhydride monomers are polymerized.

4. The method of claim 1, wherein when two types of amino acid N-carboxyanhydride monomers are polymerized, the method comprises steps:
   firstly, polymerizing one amino acid N-carboxyanhydride monomer in an organic solvent in the presence of an initiator; and
   adding another amino acid N-carboxyanhydride monomer to carry out the polymerization reaction after completing the above polymerization reaction, so as to form a block amino acid copolymer.

5. The method of claim 1, wherein when two types of amino acid N-carboxyanhydride monomers are polymerized, the method comprises steps:
   mixing two types of amino acid N-carboxyanhydride monomers in an organic solvent; and
   performing polymerization reaction in the presence of an initiator, so as to form the amino acid copolymer.

6. The method of claim 1, wherein in the amino acid N-carboxyanhydride monomer, the amino acid is a natural amino acid.

7. The method of claim 1, wherein the amino acid is selected from the group consisting of glycine, alanine, valine, leucine, isoleucine, phenylalanine, tryptophan, tyrosine, aspartic acid, asparagine, glutamic acid, lysine, glutamine, methionine, serine, threonine, cysteine, proline, histidine, arginine and derivatives derived from the above-mentioned amino acids.

8. The method of claim 1, wherein the amino acid N-carboxyanhydride monomer is L-type, D-type or DL-type.

9. The method of claim 1, wherein the amino acid N-carboxyanhydride monomer can be $\alpha$-NCA, $\beta$-NCA or $\gamma$-NCA.

10. The method of claim 1, wherein the organic solvent is selected from the group consisting of tetrahydrofuran, DMF, DMAc, acetonitrile, dioxane, and dimethylsulfoxide.

11. An amino acid polymer prepared by the method of claim 1.

12. An antibacterial material, an antitumor material, a tissue engineering scaffold, or a self-assembled material, comprising the amino acid polymer of claim 11.

13. The method of claim 1, wherein the reaction is performed in an environment without inert gas protection.

14. The method of claim 1, wherein in the amino acid N-carboxyanhydride monomer, the amino acid is an unnatural amino acid.

* * * * *